United States Patent [19]

Adair

[11] Patent Number: 4,905,670

[45] Date of Patent: Mar. 6, 1990

[54] APPARATUS FOR CERVICAL VIDEOSCOPY

[76] Inventor: Edwin L. Adair, 2800 S. University Blvd., Denver, Colo. 80210

[21] Appl. No.: 291,238

[22] Filed: Dec. 28, 1988

[51] Int. Cl.$^4$ ............................................. A61B 1/06
[52] U.S. Cl. ..................................................... 128/18
[58] Field of Search .......................... 128/3, 6, 17, 18; 354/62; 358/98

[56] References Cited

U.S. PATENT DOCUMENTS

| | | | |
|---|---|---|---|
| 3,037,505 | 6/1962 | Walden et al. | 128/17 |
| 3,789,829 | 2/1974 | Hasson | 128/17 |
| 3,789,835 | 2/1974 | Whitman | 128/18 |
| 4,210,133 | 7/1980 | Castaneda | 128/3 |
| 4,300,570 | 11/1981 | Stafl | 128/6 |
| 4,461,558 | 7/1984 | Tanikawa et al. | 354/62 |
| 4,502,468 | 3/1985 | Burgin | 128/3 |
| 4,562,832 | 1/1986 | Wilder et al. | 128/20 |
| 4,597,383 | 7/1986 | VanDerBel | 128/18 |
| 4,619,248 | 10/1986 | Walsh | 128/18 |
| 4,638,792 | 1/1987 | Burgin | 128/18 |
| 4,697,210 | 9/1987 | Toyota et al. | 358/98 |

Primary Examiner—Max Hindenburg
Attorney, Agent, or Firm—Fields, Lewis, Pittenger & Rost

[57] ABSTRACT

A simple yet highly useful cervical videoscope has been provided which can easily be used by the doctor to examine the cervix for cancerous lesions or other abnormalities. Also, because of the small size of the camera there is sufficient space between the camera and the blades of the speculum for inserting forceps and other instruments that may need to be used. By using the cervical videoscope in combination with a monochromator the physician can step the wavelength of light from one end of the light spectrum to the other until he observes florescence which identifies abnormal cells. Thereupon, he can destroy the cells by use of a laser beam. When the observes that no more florescence is occurring, then he can discontinue the operation of the laser, knowing that the lesion has been completely eradicated. Also, a channel for drawing a suction to remove smoke created by the destruction of the lesion can be provided. Finally, the camera is adjustable along a guide on the fixed blade of the speculum to focus it.

14 Claims, 2 Drawing Sheets

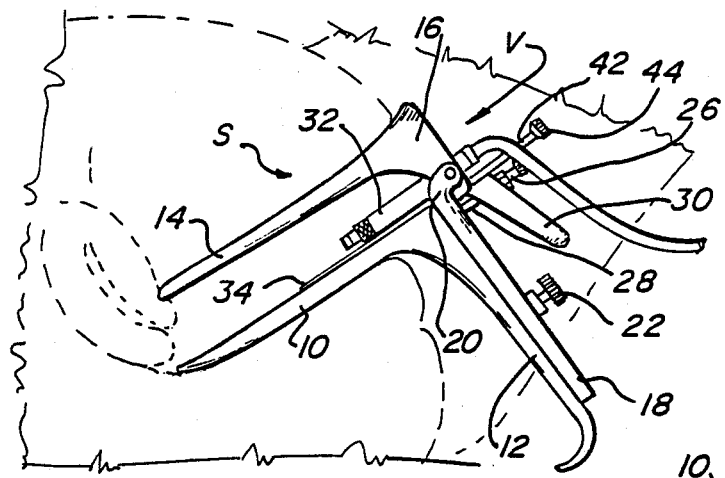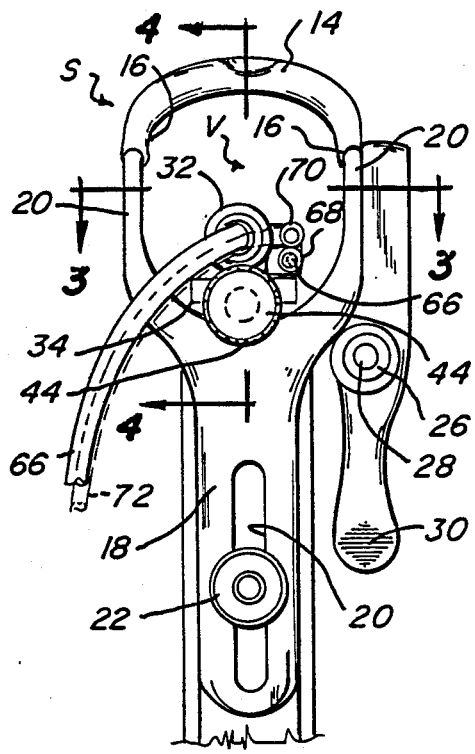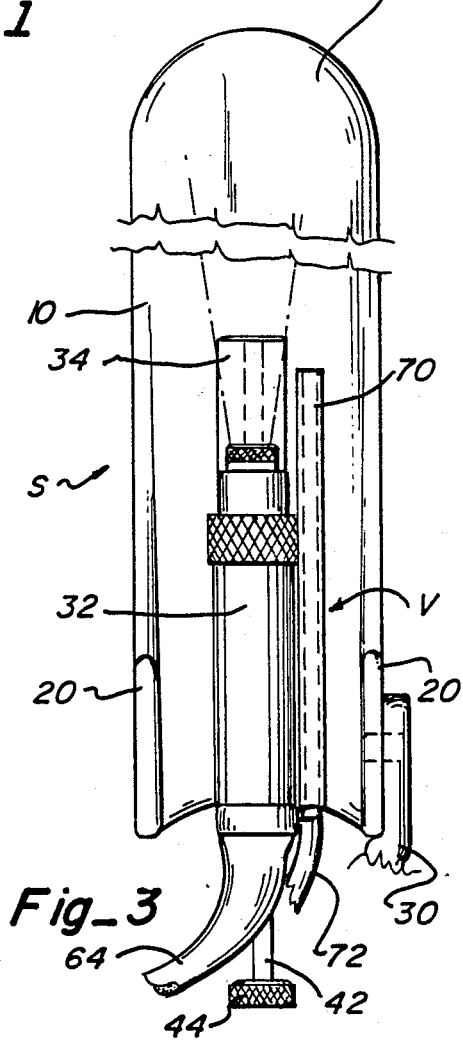

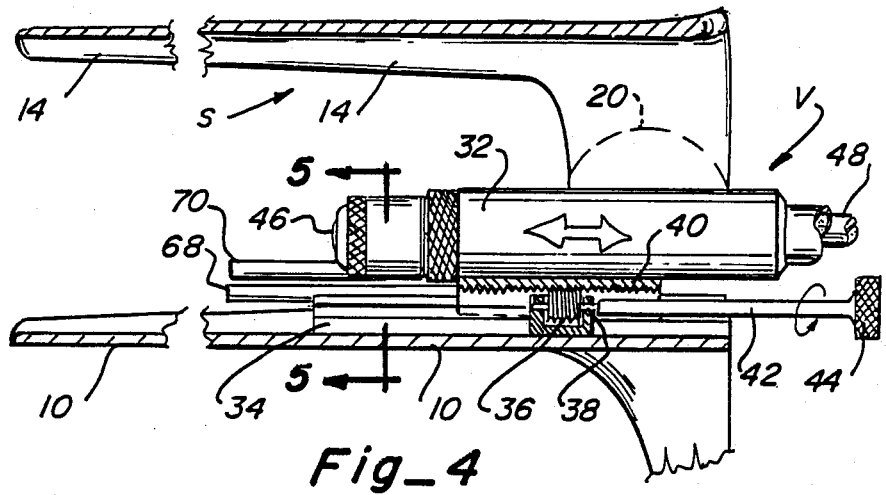
Fig_4
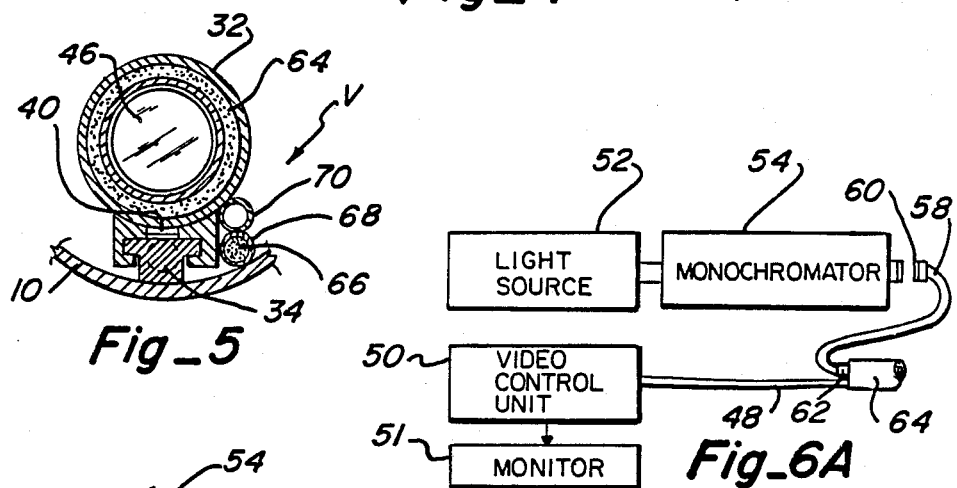
Fig_5
Fig_6A
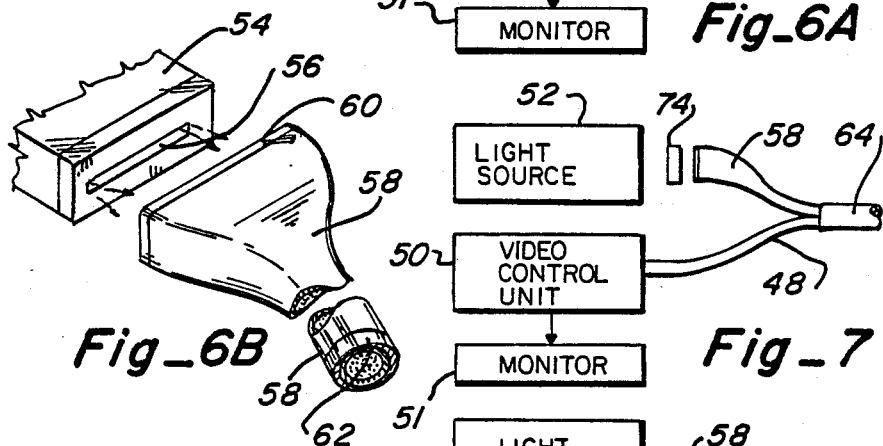
Fig_6B
Fig_7
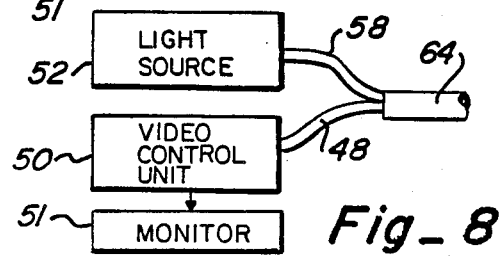
Fig_8

APPARATUS FOR CERVICAL VIDEOSCOPY

TECHNICAL FIELD

This invention relates to a cervical videoscope and particularly to one which allows inspection of the cervix under specific selected wavelength of light and provides for subsequent treatment of any lesions found on the cervix.

BACKGROUND ART

Examination of the cervix for cancer and viral infections are done now with a device called a colposcope. This device is a binocular microscope which is placed near the patient. It supplies a bright light, (white light and green light) and the operator looks through the eyepieces of the colposcope much like looking through field glasses. This is done with a vaginal speculum in place. Some of the devices have camera attachments for still picture photography. The physician looks at the tissue looking for whitened areas after treatment with 3-5% acetic acid. The acetic acid whitens tissue which is low in mucous, such as cancer cells. The physician also looks for clusters of blood vessels which may indicate new growth such as cancer. The effectiveness of this colposcopy procedure is only 85%, and this is with a very experienced physician doing the procedure. Also, the colposcope is difficult to use because of its size and weight.

Over the years various vaginal speculae have been developed. Among these are the following:

Casaneda U.S. Pat. No. 4,210,133 discloses a vaginal speculum having a microscope mounted thereon which has a light source for illumination and is longitudinally adjustable for focusing.

VanDerBel U.S. Pat No. 4,597,383 discloses a vaginal speculum having optical fiber illumination means attached thereto.

Burgin U.S. Pat. No. 4,638,792 has an adjustable speculum with an incorporated light system.

Walsh U.S. Pat. No. 4,619,248 discloses a light attachment for a speculum.

Wider et al. U.S. Pat. No. 4,562,832 illustrates in FIG. 6 a fiberoptic light pipe installed in the lower jaw of the vaginal speculum.

Burgin U.S. Pat. No. 4,502,468 has an adjustable speculum with an incorporated lighting system.

Whitman U.S. Pat. No. 3,789,835 discloses an illuminating attachment for vaginal speculum.

Stafl U.S. Pat. No. 4,300,570 has a diagnostic method of projecting the image of a cervix photograph the speculum.

Hasson U.S. Pat. No. 3,789,829 discloses a radium applicator mounted to a vaginal speculum.

Walden et al. U.S. Pat. No. 3,037,505 discloses a speculum with a spray tube carried by a jaw of the speculum.

Tanikawa et al. U.S. Pat. No. 4,461,558 discloses an endoscopic photographing apparatus applicable to all types of endoscopes and uses therefor.

Toyota et al. U.S. Pat. No. 4,697,210 discloses an endoscope for observing the interior of a cavity in a human body with the image displayed on a TV screen.

The last two patents are representative of many observation techniques available for use with endoscopes.

None of these devices have served to increase the detection rate of cancer and the early treatment thereof.

DISCLOSURE OF THE INVENTION

A cervical videoscope apparatus is provided which includes a vaginal speculum having a first fixed blade, a second blade mounted for pivotal movement toward and away from the fixed blade and spring means normally urging the second blade toward the fixed blade. The improvement includes a video camera mounted on one of the blades for viewing the cervix, means providing light to the cervix, means for focusing the camera on a selected site on the cervix and means for providing a signal from the camera to a video screen for viewing the cervix and identifying lesions thereon. The focusing means may include a track mounted longitudinally along one of the blades and means for adjusting the camera along the track for focusing. The light providing means can include a light carrier on the track for providing light to the cervix. In addition, means is provided for selecting light for illumination of the cervix at any one of a range of light frequencies. This can be broad frequency light, monochromatic light or laser light for illumination. A particularly useful light frequency has been found to be from 200 nm through 1100 nm. A suitable means for stepping sequentially through the frequencies is a monochromator. The monochromator converts light from a light source to a single frequency at an output in the form of a rectangular slit. A light carrier is provided which includes a bundle of optical fibers having a first end in a form of a rectangular collar for receiving the output from the monochromator and a circular collar at the other end for directing a round column of light onto the cervix.

A laser carrier can be provided on the track for directing a laser beam or laser fiber to vaporize lesions on the cervix. Also, a suction tube can be provided on the track to remove smoke created when the lesions are vaporized with the laser.

The invention also provides a method for locating and surgically removing lesions. This method comprises the steps of selectively illuminating the cervix with a light of different frequencies, observing the cervix as it is illuminated with each light frequency, locating lesions by their florescence or reflectance under one of the selected light frequencies and removing the lesions which have been located. The lesions may be removed by using a laser to vaporize them and the activation of the laser can be terminated in response to termination of any florescence at the lesion site.

Additional advantages of this invention will become apparent from the description which follows, taken in conjunction with the accompanying drawings.

BRIEF DESCRIPTION OF THE DRAWINGS

FIG. 1 is a side elevation of a cervical videoscope constructed in accordance with this invention and positioned for use;

FIG. 2 is an enlarged rear elevation of the cervical videoscope of FIG. 1;

FIG. 3 is a longitudinal section, taken along line 3—3 of FIG. 2; showing further details of the video camera and associated laser tube and suction tube;

FIG. 4 is a longitudinal section, taken along line 4—4 of FIG. 2, showing details of the track mounting for the video camera;

FIG. 5 is an enlarged cross-section, taken along line 5—5 of FIG. 4, showing further details of the video camera and track mechanism;

FIG. 6A is a diagrammatical view of video camera used in conjunction with a monochromator;

FIG. 6B shows details of the optical bundle connector of FIG. 6A for converting a rectangular light slit into a circular beam;

FIG. 7 is a diagrammatical view showing the video camera used with a band pass filter to provide monochromatic light; and FIG. 8 is a diagrammatical view showing the camera used directly with a light source.

BEST MODE FOR CARRYING OUT THE INVENTION

In accordance with this invention a cervical videoscope V is attached to a speculum S, as shown in FIG. 1. In use, the speculum is inserted into the vagina as shown. The speculum includes a lower fixed blade 10 having a depending handle portion 12. An upper pivotal blade 14 generally extends parallel to lower blade 10 and has depending ears 16 at the proximate by which it is pivotally mounted on a support 18. Support 18 has a yoke 20 at the upper end thereof to which ears 16 are pivoted. The lower portion of support 18 has a longitudinal slot 22 through which a thumb screw 24 extends for tightening against handle 12 to adjust the spacing of upper blade 14 from lower blade 10.

At the pivotal connection between ears 16 and yoke 20 a spring (not shown) may be provided which tends to pivot the upper blade 14 in a counterclockwise direction, as viewed in FIG. 1, so that it is moved toward fixed blade 10. However, this movement is limited by the position of nut 26 on threaded adjustment rod 28. Conveniently, rod 28 extends through a lever 30 which is fixedly attached to one of the ears 16 of upper pivotal blade 14. Thus, when nut 26 is moved outwardly along rod 28, blade 14 will pivot toward blade 10 and when nut 26 is moved inwardly along rod 28 blade 14 will pivot away from blade 10.

The videoscope V includes a camera 32 mounted on lower blade 10. A longitudinal guide member 34 is fixedly attached to stationary blade 10, as best seen in FIG. 4. Worm gear 36 is mounted within guide 34, as shown, for rotation about a pin 38. Camera 32 is provided with a rack 40 extending longitudinally therealong and attached thereto. The teeth of the rack engage worm gear 36. A control shaft 42 is attached to pin 38 and has a knob 44 for rotating worm gear 36 and thereby adjusting camera 32 longitudinally along guide 34. This provides a means for focusing the camera on the particular area of the cervix which is being investigated. Advantageously, the camera is sealed against moisture leakage into the electronics to allow soaking in a sterilizing solution between usage on different patients. It is usually backfilled with nitrogen during manufacture after air and moisture is removed in a vacuum chamber. A CCD sensor can be used to pickup the image and transmit a signal to the video monitor for processing. The camera case can be made of titanium or other metal which is substantially non-corrosive or it can be made of plastic. The camera can also be sterilized with a gas, such as ethylene oxide.

At the forward end of camera 32 is an optical lens system 46 for receiving an image from the cervix. This lens system may have zoom capabilities to provide 2X to 200X magnification. The image is projected by the camera along cable 48 to a video control unit 50 for projecting an image onto monitor 51 shown in FIG. 6A. As shown in FIG. 6A, a light source, such as xeon light source, 52 projects light through a monochromator 54. Other light sources, such as halogen, mercury vapor, mercury arc, incandescent or laser can be used. The monochromator has the ability to project light of a single wavelength from the light source 52 and to do so in stepped increments. It should have a high output with a frequency range from 200 nm to 1100 nm. By this means, a physician can look at the video monitor while stepping through each light frequency and look for fluorescing lesions on the cervix. It has been found that different types of lesions will fluoresce in response to different light wavelengths.

The light exits the monochromator 54 through a slit 56 shown in FIG. 6B and enters one end of a bundle of optical fibers 58. Conveniently, one end of optical fiber bundle 58 is mounted within a rectangular collar 60 which mates with the end of monochromator 54 for receiving light from slit 56. The other end of optical fiber bundle 58 has a circular collar 62. Collar 62 and the cable 48 for video control unit 50 connect to a cable or light carrier 64 wherein the individual optical fibers 64 are positioned around the outside of the lens system 46, as best seen in FIG. 5. Thus, the light image of selected wavelength can be directed substantially uniformly onto the surface of the cervix. As the monochromator steps the light from one end of the light spectrum to the other, a wavelength will be encountered in which cancerous lesions or lesions caused by viral infection will fluoresce and therefore will be identifiable on the video monitor.

When this occurs, these lesions can be destroyed by use of a laser beam. This is accomplished by directing the laser beam along an optical fiber 66 which extends through a channel 68 attached to guide member 34. Optical fiber 66 can be provided with steering cables (not shown) for directing the laser to the lesion cite. A KPT-532 laser, carbon dioxide laser or a YAG laser having been found to be satisfactory. Conveniently, a suction channel 70 can be provided adjacent to laser channel 68 for removing smoke caused by destruction of the lesions. This channel may be connected to a vacuum hose 72, as shown in FIG. 3.

An alternative arrangement is shown in FIG. 7 wherein a removable band pass filter 74 is provided between the light source 52 and optical fiber bundle 58 for providing selected wavelengths of light to the cervix. A band pass filter is useful when the patient is treated with a substance which will accumulate at the lesion cite and be fluorescent under a known wavelength of light. In such a case the band pass filter can be selected to transmit only the desired wavelength frequency. Suitable substances are hematoporphyrin (HPD) or a derivative thereof, such as dehematoporphyrin either (DHE), corins, pheophorbides and coumerins. Also Rhodamine-123 can be sprayed or painted on the cervix. Finally, the cite can be tagged with a monoclonal antibody.

In a still further simplified embodiment, shown in FIG. 8, the light source 52 is directly connected to optical fiber bundle 58. This embodiment can be used wherein the material at the lesion cite on the cervix will have florescence over a wide range of light wavelengths for identification of lesions.

A number of add-ons may be provided to the apparatus just described. Among these are a character generator for the patient's name, age, etc., video recorder, video printer and suitable image processors.

From the foregoing, the advantages of this invention are readily apparent. A simple yet highly useful cervical videoscope has been provided which can easily be used by the doctor to exam the cervix for cancerous lesions or other abnormalities. Also, because of the small size of the camera there is sufficient space between the camera and the blades of the speculum for inserting forceps and other instruments that may need to be used. By using the cervical videoscope in combination with a monochromator the physician can step the wavelength of light from one end of the light spectrum to the other until he observes florescence which identifies abnormal cells. Thereupon, he can destroy the cells by use of a laser beam. When he observes that no more florescence is occurring, then he can discontinue the operation of the laser, knowing that the lesion has been completely eradicated. Also, a channel for drawing a suction to remove smoke created by the destruction of the lesion can be provided. Finally, the camera is adjustable along a guide on the fixed blade of the speculum to focus it.

It should also be noted that the device may be detached from the vaginal speculum and used along with the sophisticated light sources to look for similar lesions in the rectal area or on other body surfaces.

This invention has been described in detail with reference to particular embodiments thereof, but it will be understood that various other modifications can be effected within the spirit and scope of this invention.

I claim:

1. A cervical videoscopy apparatus including a vaginal speculum having a first fixed blade, a second blade mounted for pivotal movement toward and away from said fixed blade and spring means normally urging said second blade toward said fixed blade, the improvement comprising:
   a video camera mounted on one of said blades for viewing the cervix;
   means providing light to the cervix;
   means for focusing said camera on a selected cite on the cervix; and
   means providing a signal from said camera to a video monitor for viewing the cervix and identifying lesions thereon.

2. Apparatus, as claimed in claim 1, wherein said focusing means includes:
   a track mounted longitudinally along one of said blades; and
   means for adjustably positioning said camera along said track for focusing.

3. Apparatus, as claimed in claim 2, wherein said light providing means includes:
   a light carrier on said track for providing light to the cervix.

4. Apparatus, as claimed in claim 3, wherein:
   said light carrier surrounds said camera focusing means to provide light to illuminate the cervix.

5. Apparatus, as claimed in claim 4, wherein said light providing means includes:
   means for selecting light for illumination of the cervix at any one of a range of light frequencies.

6. Apparatus, as claimed in claim 5, wherein:
   light is provided at any frequency from 200 nm through 1100 nm.

7. Apparatus, as claimed in claim 5, wherein said selecting means includes:
   means for stepping sequentially through all of the available frequencies.

8. Apparatus, as claimed in claim 7, wherein said stepping means includes;
   a monochromator for converting light from a light source to a single frequency at an output in the form of a rectangular slit; and
   means connecting said slit to said light 9. Apparatus, as claimed in claim 8, wherein said light carrier includes:
   a bundle of optical fibers having a first end and a second end;
   a rectangular collar receiving and holding said fibers at said first end of said bundle in a rectangular configuration; and
   a circular collar receiving and holding said fibers at said second end of said bundle in a circular configuration to convert the light from a slit to a round column of light for transmission to said light carrier.

10. Apparatus, as claimed in claim 5, wherein said selecting means includes:
    selected band pass filters.

11. Apparatus, as claimed in claim 5, wherein said selecting means includes:
    laser illumination of selected frequencies.

12. Apparatus, as claimed in claim 2, further including:
    a laser channel on said track positioned to direct a laser beam to vaporize lesions on the cervix seen with said camera.

13. Apparatus, as claimed in claim 12, further including:
    a suction tube on said track positioned to remove smoke when the lesions are being vaporized.

14. Apparatus, as claimed in claim 2, wherein said track and adjusting means includes:
    a guide attached to and extending longitudinally along said fixed blade;
    a worm gear rotatably mounted on said guide;
    a rack attached to and extending longitudinally of said camera which is in engagement with said worm gear; and
    a rotatable control shaft to rotate said worm gear to adjust the position of said camera along said fixed blade to focus said camera on selected portions of the cervix.

* * * * *